(12) United States Patent
Higashita et al.

(10) Patent No.: US 11,857,255 B2
(45) Date of Patent: Jan. 2, 2024

(54) OPHTHALMIC APPARATUS

(71) Applicant: Tomey Corporation, Nagoya (JP)

(72) Inventors: Risa Higashita, Nagoya (JP); Keiichiro Okamoto, Nagoya (JP)

(73) Assignee: Tomey Corporation, Nagoya (JP)

( * ) Notice: Subject to any disclaimer, the term of this patent is extended or adjusted under 35 U.S.C. 154(b) by 593 days.

(21) Appl. No.: 17/066,001

(22) Filed: Oct. 8, 2020

(65) Prior Publication Data

US 2021/0106217 A1    Apr. 15, 2021

(30) Foreign Application Priority Data

Oct. 15, 2019    (JP) .................................. 2019-188922

(51) Int. Cl.
*A61B 3/00* (2006.01)
*A61B 3/10* (2006.01)

(52) U.S. Cl.
CPC .......... *A61B 3/0025* (2013.01); *A61B 3/0041* (2013.01); *A61B 3/102* (2013.01)

(58) Field of Classification Search
CPC ..... A61B 3/0025; A61B 3/0041; A61B 3/102; G06T 2207/10016; G06T 2207/20221; G06T 2207/30041; G06T 7/33; G06T 2207/10101
USPC ....................................................... 351/206
See application file for complete search history.

(56) References Cited

U.S. PATENT DOCUMENTS

| | | |
|---|---|---|
| 2002/0186875 A1 | 12/2002 | Burmer et al. |
| 2012/0083667 A1 | 4/2012 | Isogai et al. |
| 2012/0121158 A1 | 5/2012 | Sekine et al. |
| 2012/0127428 A1 | 5/2012 | Isogai et al. |
| 2012/0200824 A1 | 8/2012 | Satake |
| 2013/0093998 A1 | 4/2013 | Bishop |
| 2014/0078466 A1 | 3/2014 | Sekine et al. |
| 2014/0167762 A1 | 6/2014 | Sugiyama |
| 2014/0204341 A1* | 7/2014 | Murase ................ A61B 3/1025 351/208 |
| 2014/0300862 A1 | 10/2014 | Perez et al. |
| 2015/0092160 A1 | 4/2015 | Chen et al. |
| 2015/0327762 A1 | 11/2015 | Isogai et al. |
| 2016/0308664 A1* | 10/2016 | Ishaug ................... H04L 7/0075 |
| 2016/0360962 A1 | 12/2016 | Okamoto et al. |
| 2017/0169588 A1 | 6/2017 | Bishop et al. |
| 2018/0289254 A1* | 10/2018 | Matsunobu .......... A61B 3/0075 |

(Continued)

FOREIGN PATENT DOCUMENTS

| | | |
|---|---|---|
| EP | 3449810 A1 | 3/2019 |
| JP | 2011-024930 A | 2/2011 |

(Continued)

*Primary Examiner* — Mohammed A Hasan
(74) *Attorney, Agent, or Firm* — Shumaker, Loop & Kendrick, LLP

(57) ABSTRACT

An ophthalmic apparatus that includes an image capturing unit configured to capture a target part of a subject eye; a processor; and a memory storing computer-readable instructions therein. The computer-readable instructions, when executed by the processor, may cause the ophthalmic apparatus to execute: acquiring a first image of the target part captured at a first timing by the image capturing unit and a second image of the target part captured at a second timing different from the first timing; and combining the first image with the second image to generate one combined image of the target part.

8 Claims, 10 Drawing Sheets

(56) References Cited

U.S. PATENT DOCUMENTS

2019/0216315 A1    6/2019  Wellenstein
2019/0355466 A1*  11/2019  Sugiyama ............. G06T 7/0012
2020/0245858 A1*   8/2020  Takeno ................ A61B 3/0041

FOREIGN PATENT DOCUMENTS

| | | |
|---|---|---|
| JP | 2012-075640 A | 4/2012 |
| JP | 2012-161427 A | 8/2012 |
| JP | 2017-000469 A | 1/2017 |
| JP | 2017-093854 A | 6/2017 |
| JP | 2018-051071 A | 4/2018 |
| JP | 6367534 B2 | 8/2018 |
| JP | 2019-042304 A | 3/2019 |
| WO | 2019005557 A1 | 1/2019 |

* cited by examiner

OPHTHALMIC APPARATUS

CROSS REFERENCE

This application claims priority to Japanese Patent Application No. 2019-188922, filed on Oct. 15, 2019, the entire contents of which are incorporated herein by reference.

TECHNICAL FIELD AND BACKGROUND

The technique disclosed herein relates to an ophthalmic apparatus.

An ophthalmic apparatus which measures a specific part (e.g., an anterior chamber angle) of a subject eye has been developed. For example, Japanese Patent Application Publication No. 2019-42304 describes an ophthalmic apparatus which captures a reflected image of an anterior chamber angle of a subject eye. In the reflected image of Japanese Patent Application Publication No. 2019-42304, an entity of the anterior chamber angle of the subject eye is captured.

SUMMARY

In the ophthalmic apparatus as described in Japanese Patent Application Publication No 2019-42304, the entity of the specific part of the subject eye is captured. As such, in order to evaluate a state of the specific part within the subject eye (e.g., the anterior chamber angle), the part to be evaluated needs to be observed over a predetermined area and possibly over even a broader area. However, depending on a degree by which an eyelid uncovers the subject eye, the part to be evaluated may only be captured within an area narrower than the predetermined area. Due to this, with the ophthalmic apparatus of Japanese Patent Application Publication No. 2019-42304, when a captured range of the specific part is narrower than the predetermined area, an image of the specific part is recaptured until the specific part is captured in an area broader than the predetermined range. Due to this, depending on a state of the subject eye, it may be needed to be recaptured many times, or may not be captured in an area broader than the predetermined area even it is recaptured.

The present disclosure discloses the technique capable of optimally acquiring a measurement result of a specific part of a subject eye.

A first ophthalmic apparatus disclosed herein may comprise: an image capturing unit configured to capture a target part of a subject eye; a processor; and a memory storing computer-readable instructions therein. The computer-readable instructions, when executed by the processor, may cause the ophthalmic apparatus to execute: acquiring a first image of the target part captured at a first timing by the image capturing unit and a second image of the target part captured at a second timing different from the first timing; and combining the first image with the second image to generate one combined image of the target part.

A second ophthalmic apparatus disclosed herein may be configured to measure a target part of a subject eye. The ophthalmic apparatus may comprise: an image capturing unit configured to capture the target part; a processor; a memory storing computer-readable instructions therein; and an informing unit. The computer-readable instructions, when executed by the processor, may cause the ophthalmic apparatus to execute: acquiring an image of the target part captured by the image capturing unit; and identifying a non-detected region in the image of the target part, the non-detected region being a region in which the target part is not detected. The informing unit may be configured to inform presence of the identified non-detected region.

DETAILED DESCRIPTION

Figure 1:
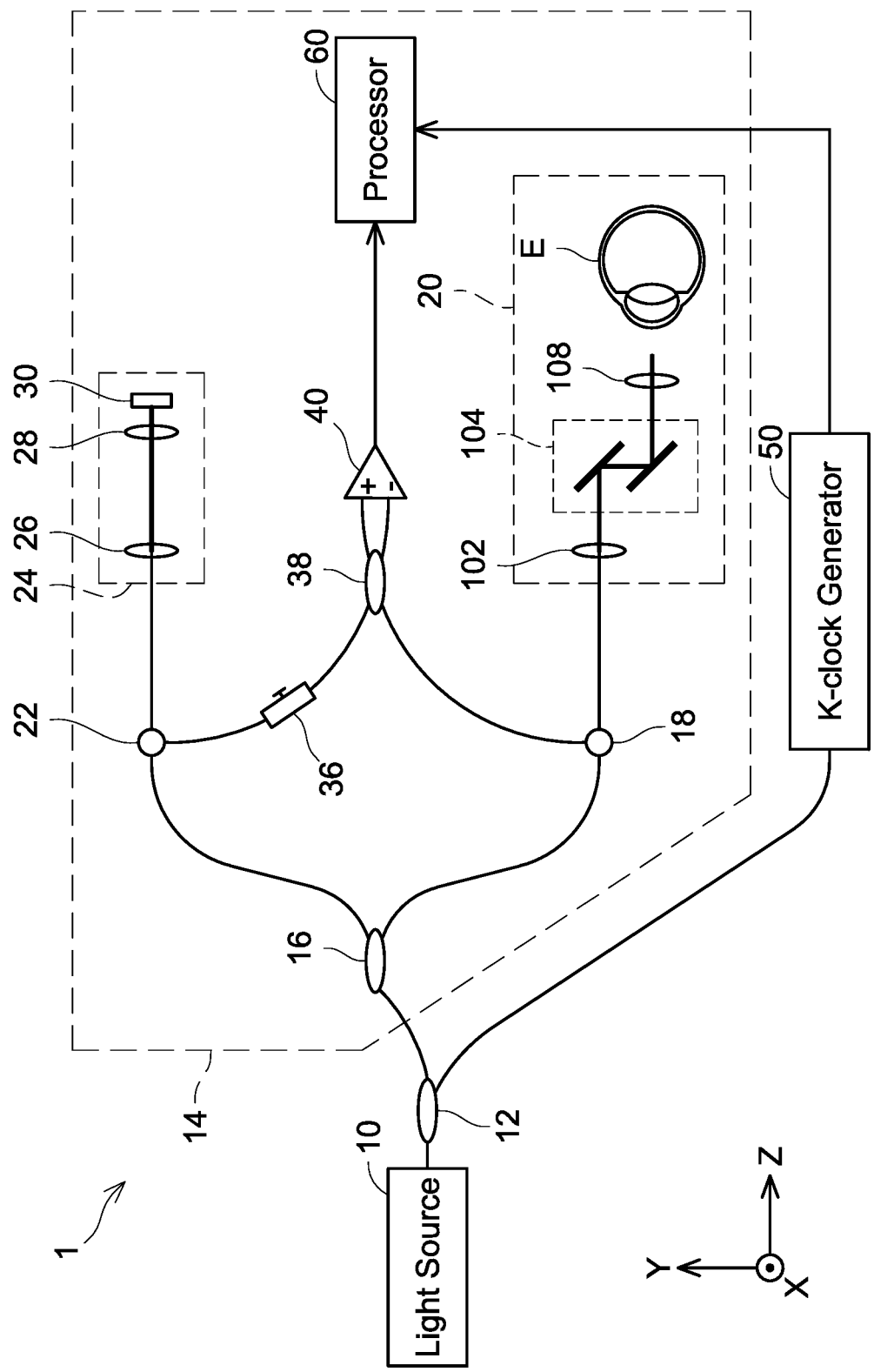
FIG. 1 shows a schematic configuration of an optical system of an ophthalmic apparatus according to an embodiment.

Representative, non-limiting examples of the present disclosure will now be described in further detail with reference to the attached drawings. This detailed description is merely intended to teach a person of skill in the art further details for practicing preferred aspects of the present teachings and is not intended to limit the scope of the present disclosure. Furthermore, each of the additional features and teachings disclosed below may be utilized separately or in conjunction with other features and teachings to provide improved ophthalmic apparatuses, as well as methods for using and manufacturing the same.

Moreover, combinations of features and steps disclosed in the following detailed description may not be necessary to practice the present disclosure in the broadest sense, and are instead taught merely to particularly describe representative examples of the present disclosure. Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Some of the features characteristic to below-described embodiments will herein be listed. It should be noted that the respective technical elements are independent of one another, and are useful solely or in combinations. The combinations thereof are not limited to those described in the claims as originally filed.

A first ophthalmic apparatus disclosed in the present may comprise: an image capturing unit configured to capture a target part of a subject eye; a processor; and a memory storing computer-readable instructions therein. The computer-readable instructions, when executed by the processor, may cause the ophthalmic apparatus to execute: acquiring a first image of the target part captured at a first timing by the image capturing unit and a second image of the target part captured at a second timing different from the first timing; and combining the first image with the second image to generate one combined image of the target part.

With the above-described ophthalmic apparatus, by combining the first and second images in each of which the target part of the subject eye is captured to generate one combined image, a portion in the first image where the target part is not captured can be supplemented by a corresponding portion in the second image, for example. Due to this, the number of times the target part of the subject eye needs to be captured to acquire a desired image can be reduced, and burden on an examinee can be reduced.

A second ophthalmic apparatus disclosed herein may be configured to measure a target part of a subject eye. The ophthalmic apparatus may comprise: an image capturing unit configured to capture the target part; a processor; a memory storing computer-readable instructions therein; and an informing unit. The computer-readable instructions, when executed by the processor, may cause the ophthalmic apparatus to execute: acquiring an image of the target part captured by the image capturing unit; and identifying a non-detected region in the image of the target part, the non-detected region being a region in which the target part is not detected. The informing unit may be configured to inform presence of the identified non-detected region.

In the above-described ophthalmic apparatus, by the informing unit informing the presence of the non-detected region in the captured image, an examiner can identify where the non-detected region is positioned. Due to this, for example, the examiner can recapture an entirety of the target part so that the non-detected region is included therein, by which the number of times the target part of the subject eye needs to be captured to acquire the desirable image can be reduced, and burden on the examinee can be reduced.

The ophthalmic apparatus disclosed herein may further comprise a display unit configured to display images of the target part including the combined image of the target part. According to such a configuration, the combined image of the target part can be visually identified.

In the ophthalmic apparatus disclosed herein, the first image may be an image that is captured when an eyelid uncovers a first region of the target part. The second image may be an image that is captured when the eyelid uncovers a second region of the target part. The second region may be different from the first region. According to such a configuration, since a degree by which the eyelid uncovers the subject eye when the first image is captured (a state where the eyelid uncovers the first region) is different from a degree by which the eyelid uncovers the subject eye when the second image is captured (a state where the eyelid uncovers the second region), a captured region of the target part in the first image is different from that in the second image. By combining these images, an image including the target part in a broader area can be acquired.

In the ophthalmic apparatus disclosed herein, in the combining, the first image and the second image may be combined by matching positions of a common portion captured respectively in the first image and the second. According to such a configuration, by matching the positions of the common portion between the first image and the second image, displacement caused upon combining the first and second images can be suppressed.

In the ophthalmic apparatus disclosed herein, the computer-readable instructions, when executed by the processor, may further cause the ophthalmic apparatus to execute identifying a non-detected region in the first image, the non-detected region being a region in which the target part is not detected. In the combining, a portion of the second image corresponding to the non-detected region of the first image may be combined with a portion of the first image where the target part is detected. According to such a configuration, by combining the portion of the second image corresponding to the non-detected region of the first image with the portion of the first image where the target part is detected, a portion of the first image where the target part is not detected can be replaced with the corresponding portion of the second image. Due to this, an image including the target region in a broader area can be acquired.

The ophthalmic apparatus disclosed herein may further comprise an informing unit configured to inform presence of the non-detected region when an image captured by the image capturing unit includes the non-detected region. According to such a configuration, when the target part of the subject eye is captured by the image capturing unit and the captured image includes the non-detected region, the informing unit informs the presence of the non-detected region, by which the examiner can identify where the non-detected region, which needs to be recaptured, is positioned. Due to this, for example, the examiner can recapture an image such that the image includes the non-detected region, by which an image more suitable as an image to be combined can be acquired.

In the ophthalmic apparatus disclosed herein, the informing unit may be further configured to: instruct to open an eyelid to uncover an upper part of the subject eye when the non-detected region is located in the upper part of the subject eye; instruct to open the eyelid to uncover a lower part of the subject eye when the non-detected region is located in the lower part of the subject eye; and instruct to open the eyelid to uncover the upper and lower parts of the subject eye when the non-detected regions are located in the upper and lower parts of the subject eye. According to such a configuration, the informing unit can instruct the examiner so that a more suitable image can be acquired depending on a position of the non-detected region.

EMBODIMENT

Hereinbelow, an ophthalmic apparatus 1 according to an embodiment will be described. The ophthalmic apparatus 1 is configured to capture tomographic images of an anterior eye part of a subject eye E by using an Optical Coherence Tomography (OCT). As shown in FIG. 1, the ophthalmic apparatus 1 includes a light source 10, an interference optical system 14 configured to cause reflected light reflected from the subject eye E and reference light to interfere with each other, and a K-clock generator 50 configured to generate K-clock signals.

The light source 10 is a wavelength-sweeping light source, and is configured to change a waveform of the light emitted therefrom in a predetermined cycle. When the wavelength of the light emitted from the light source 10 changes, a reflected position of reflected light that interferes with the reference light, among reflected light from respective parts of the subject eye E in a depth direction, changes in the depth direction of the subject eye E in accordance with the wavelength of the emitted light. Due to this, it is possible to identify positions of the respective parts (such as a cornea and a crystalline lens) inside the subject eye E by measuring the interference light while changing the wavelength of the emitted light.

The light outputted from the light source 10 is inputted to a fiber coupler 12 through an optical fiber. The light inputted to the fiber coupler 12 is split in the fiber coupler 12, and the split light is outputted to a fiber coupler 16 and the K-clock generator 50 through optical fibers. The K-clock generator 50 will be described later.

The interference optical system 14 includes a measurement optical system configured to irradiate inside of the subject eye E with light from the light source 10 and generate reflected light therefrom, a reference optical system configured to generate reference light from the light of the light source 10, and a balance detector 40 configured to detect interference light that is a combination of the reflected light guided by the measurement optical system and the reference light guided by the reference optical system.

The measurement optical system is constituted of the fiber coupler 16, a circulator 18, and a scanning-alignment optical system 20. The light outputted from the light source 10 and inputted to the fiber coupler 16 through the fiber coupler 12 is split in the fiber coupler 16 into measurement light and reference light, and these light are outputted therefrom. The measurement light outputted from the fiber coupler 16 is inputted to the circulator 18 through an optical fiber. The measurement light inputted to the circulator 18 is outputted to the scanning-alignment optical system 20. The scanning-alignment optical system 20 is configured to irradiate the subject eye E with the measurement light outputted from the circulator 18 and to output reflected light from the subject eye E to the circulator 18. The reflected light inputted to the circulator 18 is inputted to one of inputs of a fiber coupler 38. The scanning-alignment optical system 20 will be described later in detail.

The reference optical system is constituted of the fiber coupler 16, a circulator 22, and a reference unit 24. The reference light outputted from the fiber coupler 16 is inputted to the circulator 22 through an optical fiber. The reference light inputted to the circulator 22 is outputted to the reference unit 24. The reference unit 24 is constituted of collimator lenses 26, 28 and a reference mirror 30. The reference light outputted to the reference unit 24 is reflected by the reference mirror 30 through the collimator lenses 26, 28, and is outputted from the reference unit 24 through the collimator lenses 26, 28 again. The reference light outputted from the reference unit 24 is outputted to the circulator 22. The collimator lens 28 and the reference mirror 30 are each configured to be moved forward and rearward relative to the collimator lens 26 by a second driver 54 (see FIG. 3). When the second driver 54 moves the collimator lens 28 and the reference mirror 30, an optical path length of the reference optical system changes. Due to this, the optical path length of the reference optical system can be adjusted to be substantially equal to an optical path length of the measurement optical system. The reference light inputted to the circulator 22 is inputted to another input of the fiber coupler 38 through a polarized wave controller 36. The polarized wave controller 36 is an element configured to control polarization of the reference light to be inputted to the fiber coupler 38. As the polarized wave controller 36, a configuration such as a paddle type or an inline type used in known ophthalmic apparatuses can be used, thus a detailed description thereof will be omitted.

The fiber coupler 38 is configured to combine the reflected light from the subject eye E and the reference light that were inputted thereto to generate interference light. The fiber coupler 38 is further configured to split the generated interference light into two interference light having phases that differ by 180 degrees from each other, and input them to the balance detector 40. The balance detector 40 is configured to execute a process for differential amplification and a process for reducing noise on the two interference light having the phases that differ by 180 degrees, which were inputted from the fiber coupler 38, to convert them into electric signals (interference signals). The balance detector 40 is configured to output the interference signals to a processor 60.

Here, a configuration of the scanning-alignment optical system 20 will be described with reference to FIG. 2. The scanning-alignment optical system 20 includes a scanning optical system, an anterior-eye-part image capturing system, a fixation target optical system, and an alignment optical system.

Figure 2:
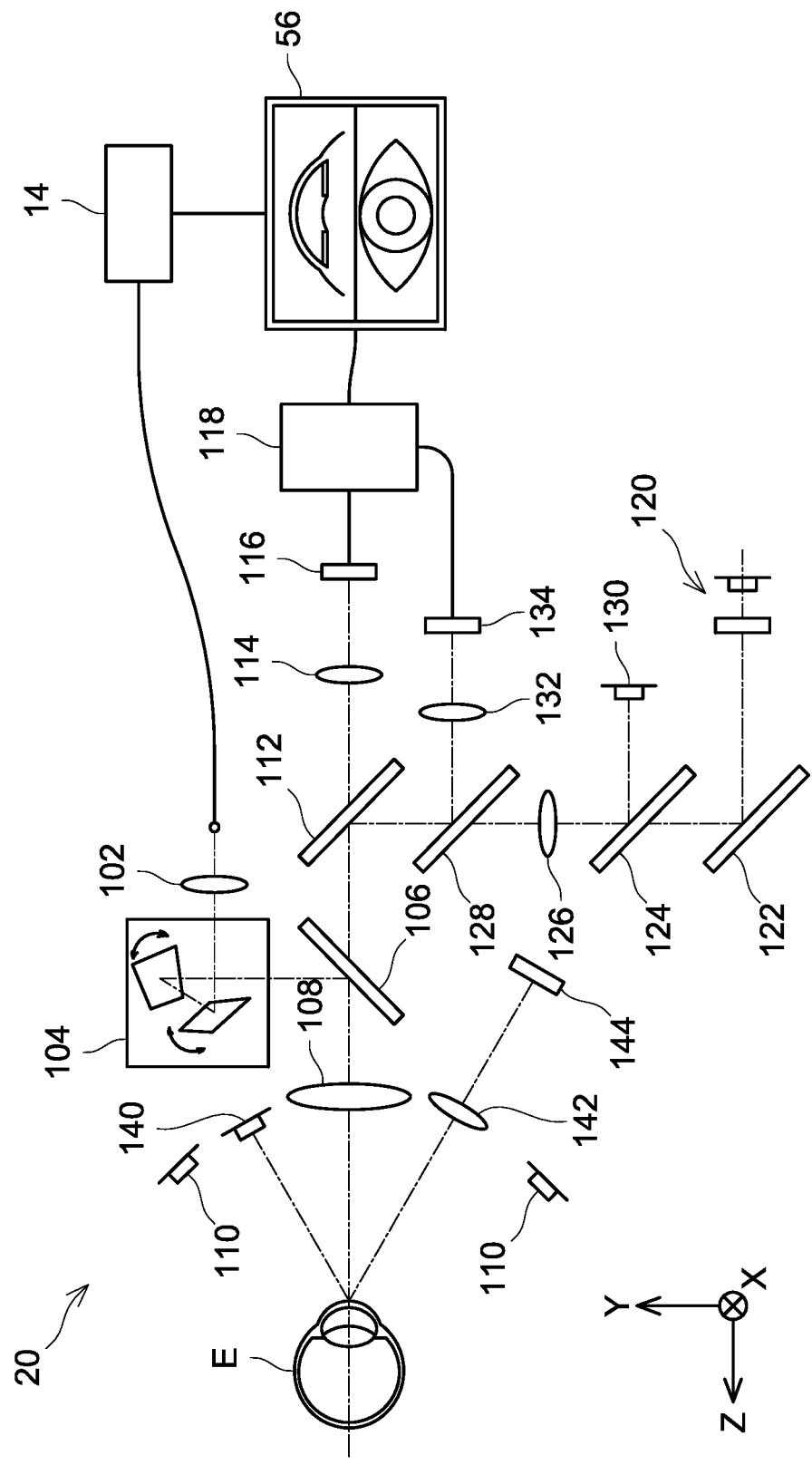
FIG. 2 shows a schematic configuration of a scanning-alignment optical system.

As shown in FIG. 2, the scanning optical system includes a collimator lens 102, a Galvano scanner 104, a hot mirror 106, and an object lens 108. The measurement light outputted from the circulator 18 (see FIG. 1) is emitted to the Galvano scanner 104 through the collimator lens 102. The Galvano scanner 104 is configured to be tilted by a first driver 52 (see FIG. 3), and a position irradiated with the measurement light in the subject eye E is scanned by the first driver 52 tilting the Galvano scanner 104. The hot mirror 106 is irradiated with the measurement light emitted from the Galvano scanner 104 and the measurement light is reflected there at an angle of 90 degrees. The measurement light with which the hot mirror 106 was irradiated is provided to the subject eye E through the object lens 108. Reflected light from the subject eye E is inputted to the circulator 18 after passing through the object lens 108, the hot mirror 106, the Galvano scanner 104, and the collimator lens 102 along a reversed path from the above.

The anterior-eye-part image capturing system includes two illuminating light sources 110, the object lens 108, the hot mirror 106, a cold mirror 112, an imaging lens 114, a CCD camera 116, and an optical controller 118. The two illuminating light sources 110 are configured to irradiate a front side of the subject eye E with illumination light in a visible range. Reflected light from the subject eye E travels through the object lens 108, the hot mirror 106, the cold mirror 112 and the imaging lens 114 and is inputted to the CCD camera 116. Due to this, a front image of the subject eye E is captured. Data of the captured image is subjected to image processing by the optical controller 118 and is displayed on a touch panel 56.

The fixation target optical system includes a fixation target light source 120, cold mirrors 122, 124, a relay lens 126, a half mirror 128, the cold mirror 112, the hot mirror 106, and the object lens 108. Light from the fixation target light source 120 travels through the cold mirrors 122, 124, the relay lens 126 and the half mirror 128, and is reflected on the cold mirror 112. The light reflected on the cold mirror 112 travels through the hot mirror 106 and the object lens 108, and the subject eye E is irradiated with the light. By causing an examinee to fix his/her vision at the light from the fixation target light source 120, an eyeball (that is, the subject eye E) can be held still as much as possible.

The alignment optical system is constituted of an XY-direction position detection system and a Z-direction position detection system. The XY-direction position detection system is used to detect positions of the subject eye E (to be more precise, a corneal apex thereof) in XY directions (that is, positional displacements thereof in up-down and right-left directions relative to the ophthalmic apparatus 1). The Z-direction position detection system is used to detect a position of the corneal apex of the subject eye E in a front-rear direction (a Z direction).

The XY-direction position detection system includes an XY-position detection light source 130, the cold mirror 124, the relay lens 126, the half mirror 128, the cold mirror 112, the hot mirror 106, the object lens 108, an imaging lens 132, and a position sensor 134. The XY-position detection light source 130 is configured to emit alignment light for position detection. The alignment light emitted from the XY-position detection light source 130 is reflected on the cold mirror 124, travels through the relay lens 126 and the half mirror 128, and is reflected on the cold mirror 112. The light reflected on the cold mirror 112 travels through the hot mirror 106 and the object lens 108, and the anterior eye part (cornea) of the subject eye E is irradiated with the light.

Since a corneal surface of the subject eye E is spherical, the alignment light is reflected on the corneal surface so as to form a bright spot image on an inner side with respect to the corneal apex of the subject eye E. The reflected light from this corneal surface enters the object lens 108 and is reflected on the cold mirror 112 through the hot mirror 106. The reflected light reflected on the cold mirror 112 is reflected on the half mirror 128 and is inputted to the position sensor 134 through the imaging lens 132. A position of the corneal apex (that is, its position in X and Y directions) is detected by the position sensor 134 detecting a position of the bright spot.

The detection signal of the position sensor 134 is inputted to the processor 60 through the optical controller 118. In this case, alignment is set between the position sensor 134 and the anterior-eye-part image capturing system, and a predetermined (regular) image acquisition position for the corneal apex (a position thereof to be tracked upon acquiring tomographic images) is set. The regular image acquisition position for the corneal apex is, for example, a point that matches a center position of an image captured by the CCD camera 116. The processor 60 is configured to calculate positional displacement amounts of the detected corneal apex (bright point) in the X and Y directions relative to the regular image acquisition position based on the detection of the position sensor 134.

The Z-direction position detection system includes a Z-position detection light source 140, an imaging lens 142, and a line sensor 144. The Z-position detection light source 140 is configured to irradiate the subject eye E with light for detection (slit light or spot light) from an oblique direction with respect to the subject eye E. Reflected light in the oblique direction from the cornea of the subject eye E enters the line sensor 144 through the imaging lens 142. At this occasion, an incident position of the reflected light entering the line sensor 144 varies depending on the position of the subject eye E in the front-rear direction (Z-direction) relative to the ophthalmic apparatus 1. Due to this, the position of the subject eye E in the Z direction relative to the ophthalmic apparatus 1 is detected by detecting the incident position of the reflected light. The detection signal of the line sensor 144 is inputted to the processor 60.

The K-clock generator 50 (see FIG. 1) is configured to optically generate sample clock (K-clock) signals from the light of the light source 10 to sample the interference signals at a regular interval frequency (frequency interval that is equalized with respect to light frequency). Further, the generated K-clock signals are outputted toward the processor 60. Due to this, the processor 60 samples the interference signals based on the K-clock signals, by which distortion in the interference signals can be suppressed and deterioration in resolution can be prevented. In the present embodiment, the interference signals that were sampled at timings defined by the K-clock signals are inputted to the processor 60, however, no limitation is placed to this configuration. For example, the processor 60 may execute a process to scale data sampled at a predetermined time interval by using a function indicating a frequency with respect to a preset sweep time, or a sweep profile that is acquired simultaneously therewith.

Figure 3:
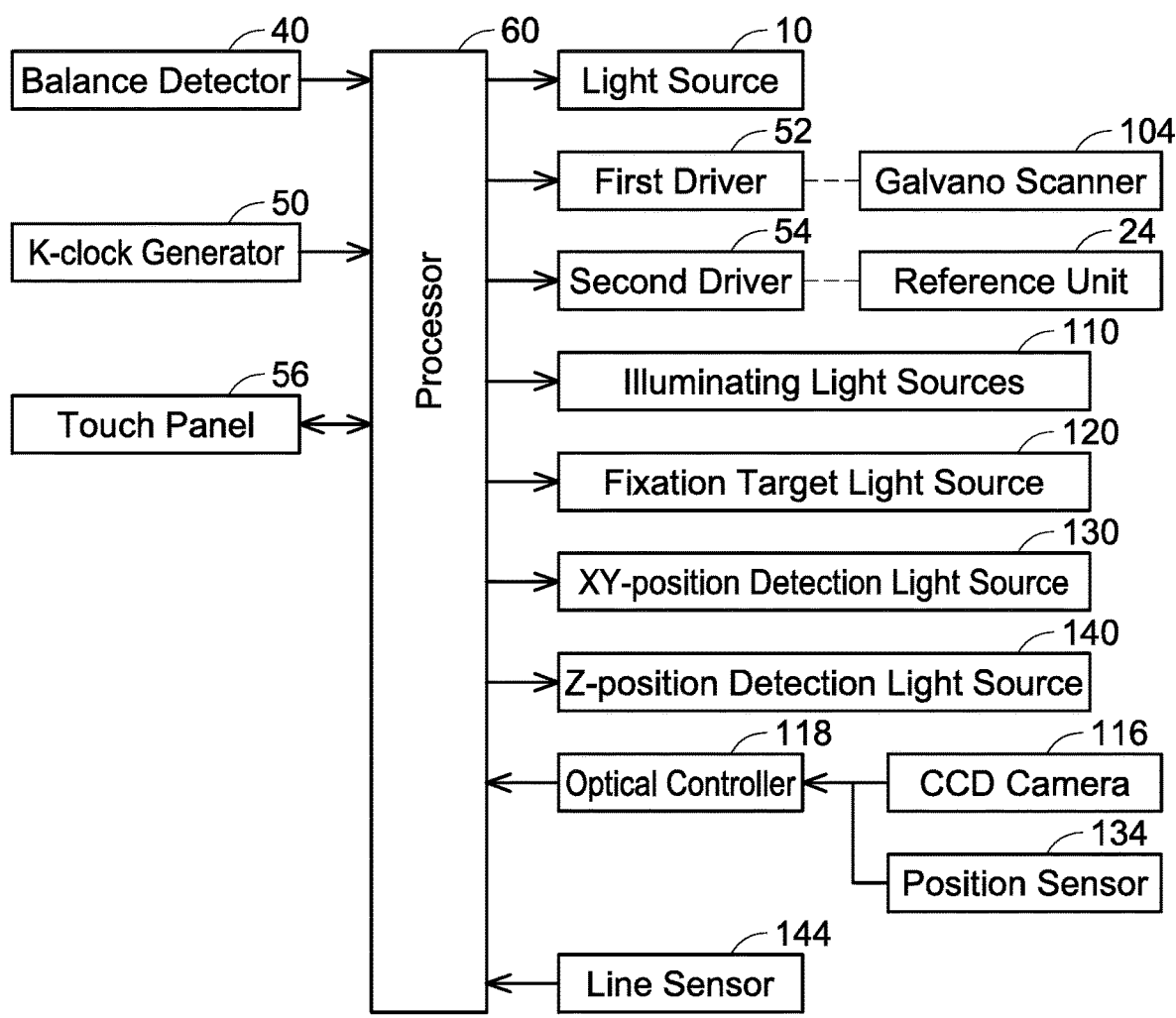
FIG. 3 is a block diagram showing a control system of the ophthalmic apparatus according to the embodiment.

Next, a configuration of a control system of the ophthalmic apparatus 1 according to the present embodiment will be described. As shown in FIG. 3, the ophthalmic apparatus 1 is controlled by the processor 60. The processor 60 is constituted of a microcomputer (microprocessor) constituted of a CPU, a ROM, a RAM, and the like. The processor 60 is connected with the light source 10, the first driver 52, the second driver 54, the illuminating light sources 110, the fixation target light source 120, the XY-position detection light source 130, the Z-position detection light source 140, the optical controller 118, the line sensor 144, the balance detector 40, the K-clock generator 50, and the touch panel 56.

The processor 60 is configured to control on/off of the light source 10 and to drive the Galvano scanner 104 and the reference unit 24 by controlling the first driver 52 and the second driver 54. Further, the interference signals corresponding to intensities of the interference light detected by the balance detector 40 and the K-clock signals generated by the K-clock generator 50 are inputted to the processor 60. The processor 60 is configured to sample the interference signals from the balance detector 40 based on the K-clock signals. Further, the processor 60 executes Fourier transform on the sampled interference signals to identify positions of respective parts (such as the cornea, an anterior chamber, and a crystalline lens) of the subject eye E. Data and calculation results inputted to the processor 60 are stored in a memory (not shown).

Further, the processor 60 is configured to control on/off of the illuminating light sources 110, the fixation target light source 120, and the XY-position detection light source 130. The front image of the subject eye E captured by the CCD camera 116 and processed by the optical controller 118 and the position of the corneal apex (bright point) detected by the position sensor 134 via the optical controller 118 are inputted to the processor 60. The processor 60 is configured to calculate the displacement amounts of the corneal apex (bright point) in the XY directions based on the front image of the subject eye E and the position of the corneal apex (bright point) that were inputted. The detection signal of the line sensor 144 is inputted to the processor 60, and the processor 60 is configured to calculate the displacement amount of the subject eye E in the Z direction relative to the ophthalmic apparatus 1. Based on the positional displacement amounts of the corneal apex (bright point) in the X and Y directions detected by the XY-direction position detection system and the positional displacement amount of the subject eye E in the Z direction detected by the Z-direction position detection system, the processor 60 controls a main driver (not shown) such that the aforementioned positional displacement amounts all become 0 and moves a main body of the ophthalmic apparatus 1 relative to a stage (not shown).

Further, the processor 60 controls the touch panel 56. The touch panel 56 is a display unit for providing the examiner with a variety of information related to a measurement result and an analysis result of the subject eye E, and is also a user interface configured to receive instructions and information from the examiner. For example, the touch panel 56 can display an image of the anterior eye part, tomographic images, the analysis result, and an instruction on presence of a non-detected region 72 to the examiner (to be described later) generated by the processor 60. Further, various settings for the ophthalmic apparatus 1 can be imputed to the touch panel 56. Although the ophthalmic apparatus 1 of the present embodiment includes the touch panel 56, the disclosure herein is not limited to such a configuration. The ophthalmic apparatus may have a configuration which enables display and input of the aforementioned information, and may include a monitor and an input device (e.g., a mouse and a keyboard).

Processes of acquiring an image of a scleral spur SS of the subject eye E will be explained with reference to FIGS. 4 to 11. For example, when a state of an angle recess is evaluated by using tomographic images, the tomographic images need to be captured so that the images include the angle recess. However, when an eyelid insufficiently uncovers the subject eye E, the angle recess on an upper side or on a lower side of the subject eye E may not be captured due to being covered by the eyelid. The ophthalmic apparatus 1 according to the present embodiment is configured to acquire an image including an entirety of the angle recess of the subject eye E in its circumferential direction. Hereafter, it is determined that an image includes the angle recess when the image includes the scleral spur SS positioned at an anterior chamber angle part. As such, processes of acquiring an image which includes an entirety of the scleral spur SS of the subject eye E in its circumferential direction will be described.

Figure 4:
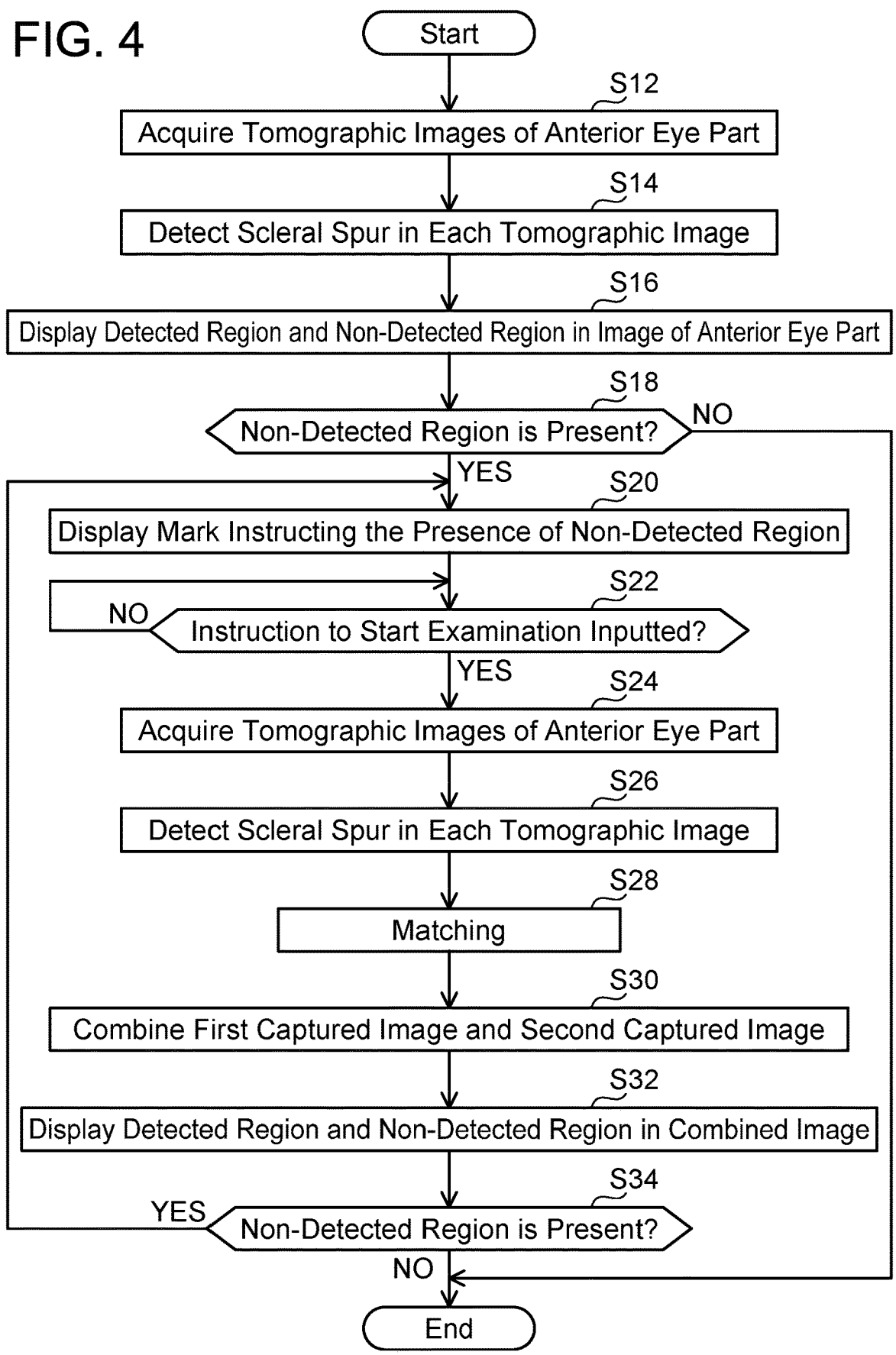
FIG. 4 is a flow chart showing an example of processes for acquiring an image of a scleral spur of a subject eye.

Firstly, as shown in FIG. 4, the processor 60 acquires tomographic images of the anterior eye part of the subject eye E (S12). The process of acquiring tomographic images of the anterior eye part of the subject eye E is executed according to the following procedure. Firstly, when the examiner inputs an instruction to start an examination on the touch panel 56, the processor 60 executes alignment between the subject eye E and the ophthalmic apparatus 1. The alignment is executed based on the displacement amounts in the XY directions and the Z direction detected by the alignment optical system. Specifically, the processor 60 moves the main body of the ophthalmic apparatus 1 relative to the stage (not shown) so that the positional displacement amounts of the corneal apex (bright point) in the X and Y directions detected by the XY-direction position detection system and the positional displacement amount of the subject eye E in the Z direction detected by the Z-direction position detection system all become 0.

Figure 5A:
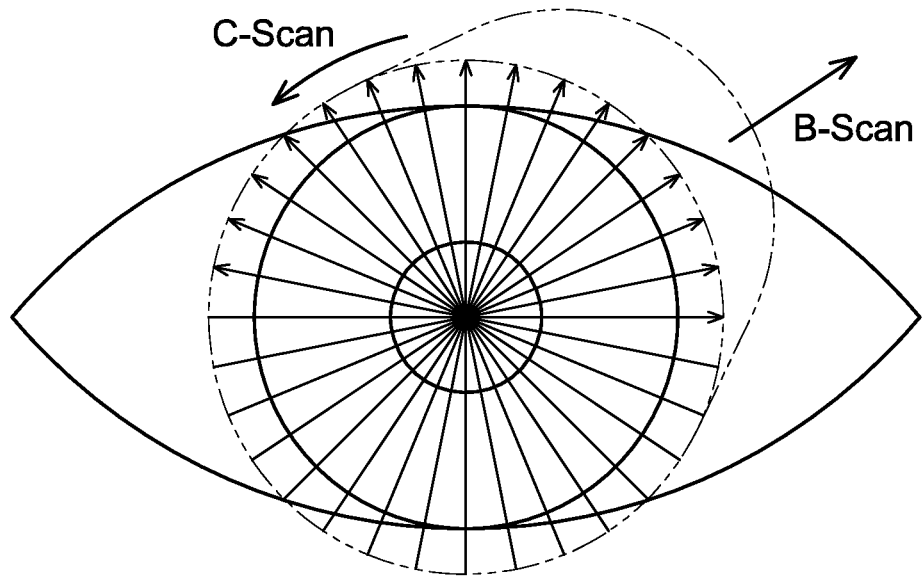
FIGS. 5A and 5B are diagrams for explaining a radial scanning scheme.
Figure 5B:
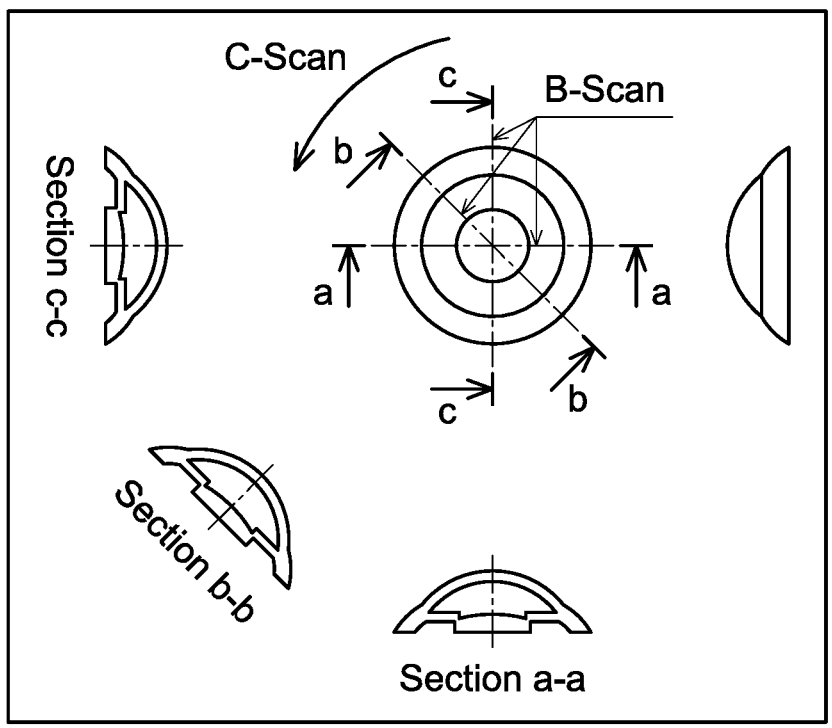
Figure 6A:
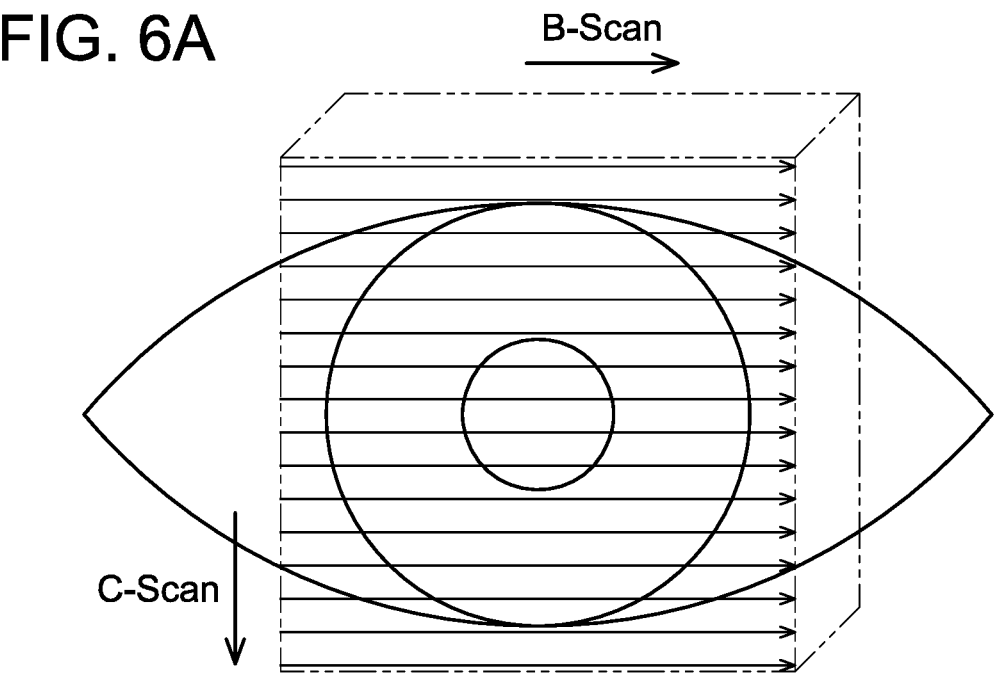
FIGS. 6A and 6B are diagrams for explaining a raster scanning scheme.
Figure 6B:
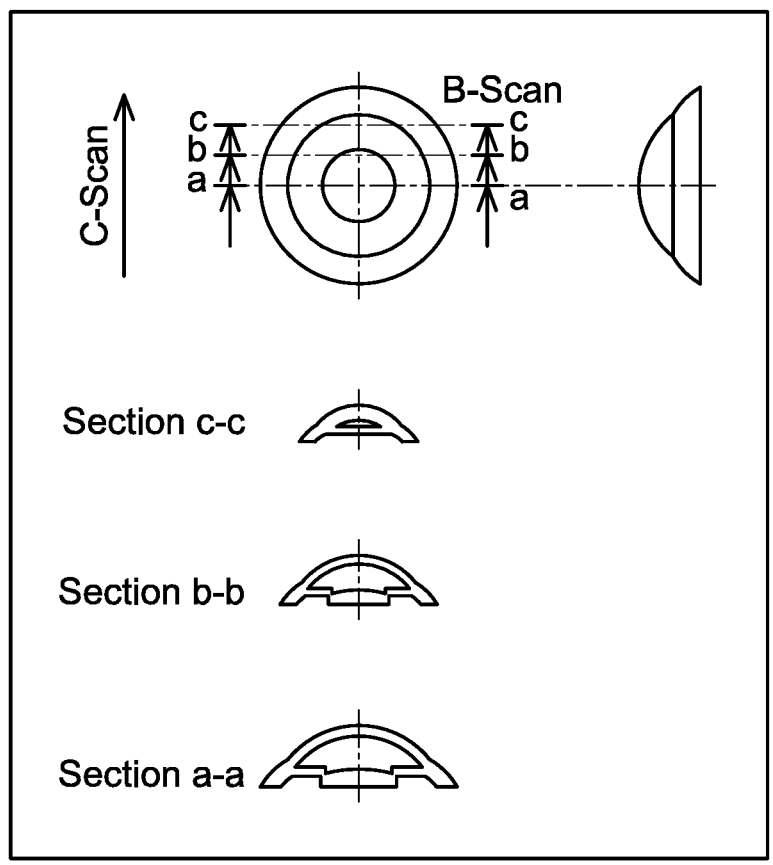

When the alignment is completed, the processor 60 captures tomographic images of the anterior eye part of the subject eye E. In this embodiment, the measurement of the anterior eye part of the subject eye E in step S12 is executed according to a radial scanning scheme. Due to this, the tomographic images of the anterior eye part are acquired over an entire region thereof. That is, as shown in FIG. 5, the tomographic images are captured with B-scan directions set in radial directions from the corneal apex of the subject eye E and a C-scan direction set in a circumferential direction thereof. In this embodiment, the tomographic images are captured in 128 directions radially (specifically, in 128 directions at regular intervals in the circumferential direction) according to the radial scanning scheme. The processor 60 records data of the acquired (captured) tomographic images in the memory. A method of capturing tomographic images of the anterior eye part is not limited to the radial scanning scheme. Any method may be adopted so long as it is able to acquire tomographic images of the anterior eye part over an entire region thereof, and for example, the images may be captured according to a raster scanning scheme. That is, as shown in FIG. 6, the tomographic images may be captured with the B-scan direction in a horizontal direction and the C-scan direction set in a vertical direction relative to the subject eye E.

Figure 7A:
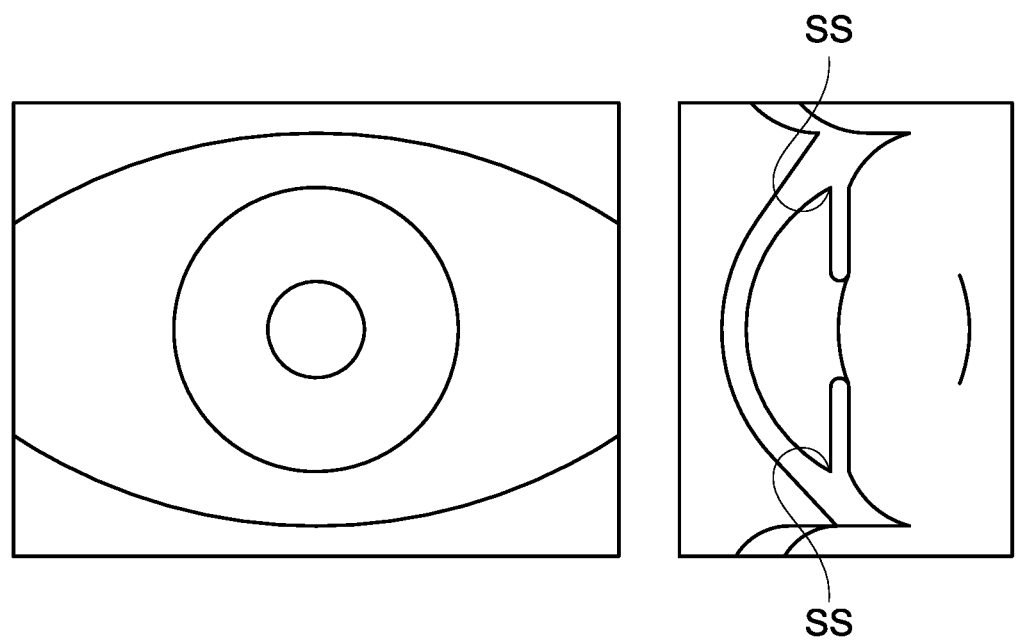
FIG. 7A schematically shows an image of an anterior eye part and its tomographic image captured in a state where an eyelid sufficiently uncovers the subject eye, and FIG. 7B schematically shows a state where a position of a detected region and the scleral spur are overlapped on FIG. 7A and displayed as such.
Figure 8A:
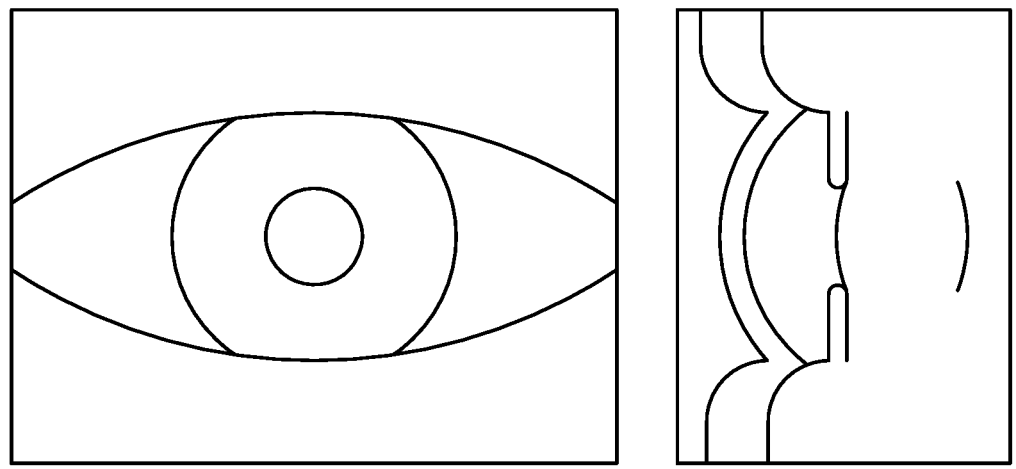
FIG. 8A schematically shows an image of the anterior eye part and its tomographic image captured in a state where the eyelid does not sufficiently uncover an upper part or lower part of the subject eye, and FIG. 8B schematically shows a state where positions of the detected regions, non-detected regions, and the scleral spur are overlapped on FIG. 8A and displayed as such.

In step S12, when the tomographic images of the anterior eye part of the subject eye E are acquired, the processor 60 detects the scleral spur SS in each of the tomographic images (S14). The scleral spur SS in each of the tomographic images can be detected by using a well-known method, thus the method is not particularly limited. For example, the scleral spur SS in each of the tomographic images may be detected by the examiner inputting position(s) of the scleral spur SS to the two-dimensional tomographic image displayed on the touch panel 56, or may be detected by the processor 60 executing a well-known image processing program (for example, program for detecting a posterior surface of a cornea and an anterior surface of an iris and determining a boundary therebetween). As shown in FIG. 7A, when the eyelid sufficiently uncovers the subject eye E upon capturing, the scleral spur SS is captured at two points in all the tomographic images. In this case, the scleral spur SS is detected at two points in all the tomographic images. On the other hand, as shown in FIG. 8A, when the eyelid does not sufficiently uncover the subject eye E upon capturing images, the scleral spur SS at an upper part and a lower part of the subject eye E (or the scleral spur SS at one of the upper part or the lower part of the subject eye E) may not be captured. In this case, the scleral spur SS cannot be detected in image(s) including the upper and lower parts (or one of the upper part or the lower part) of the subject eye E covered by the eyelid among a plurality of tomographic images.

Next, the processor 60 overlaps region(s) 70 where the scleral spur SS has been detected and region(s) 72 where the scleral spur SS has not been detected on the image of the anterior eye part of the subject eye E and displays the resulting image on the touch panel 56 (S16). Specifically, the processor 60 overlaps circumferential region(s) 70 where the scleral spur SS has been detected (hereinbelow simply referred to as "detected region(s) 70") and circumferential region(s) 72 where the scleral spur SS has not been detected (hereinbelow simply referred to as "non-detected region(s) 72") on the image of the anterior eye part and display the resulting image.

Figure 7B:
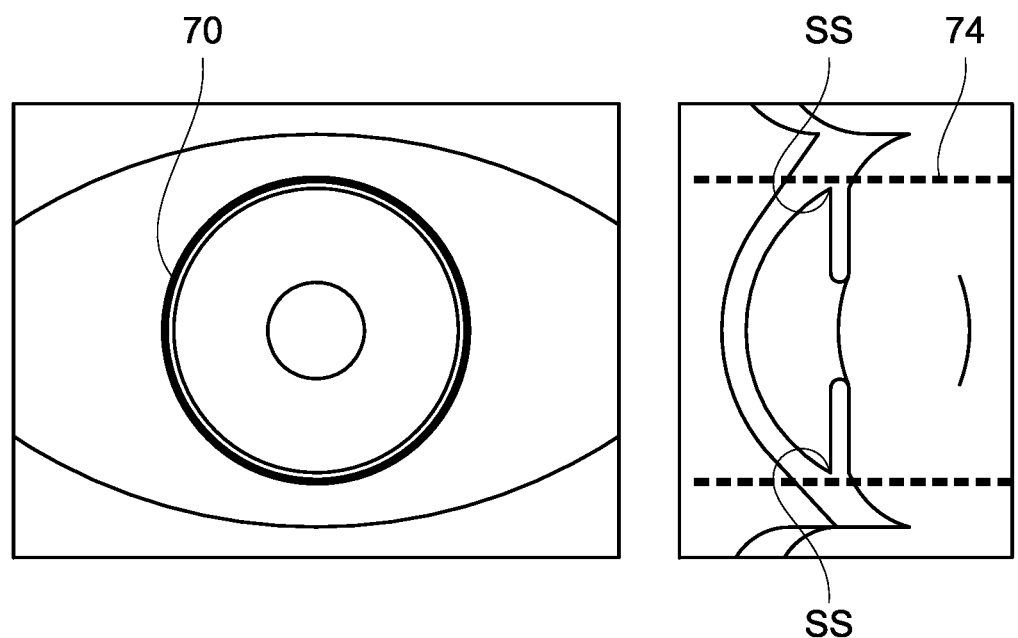

As shown in FIG. 7B, when the scleral spur SS has been detected in all the tomographic images in step S14, the detected region 70 is displayed over its entire circumference, and the non-detected region 72 is not displayed. At this occasion, the detected region 70 may be displayed by connecting the scleral spur SS detected in adjacent tomographic images by line segments, or may be displayed as a reference ellipse including circle (hereinafter referred to as "reference circle") calculated based on positions of the detected scleral spur SS. Since a method of calculating the above reference circle is identical with a well-known calculation method described in Japanese Patent No. 6367534, for example, thus the detailed explanation thereof will be omitted. Hereinbelow, this method of calculating the reference circle may be referred to as "SS entire circumference fitting".

Figure 8B:
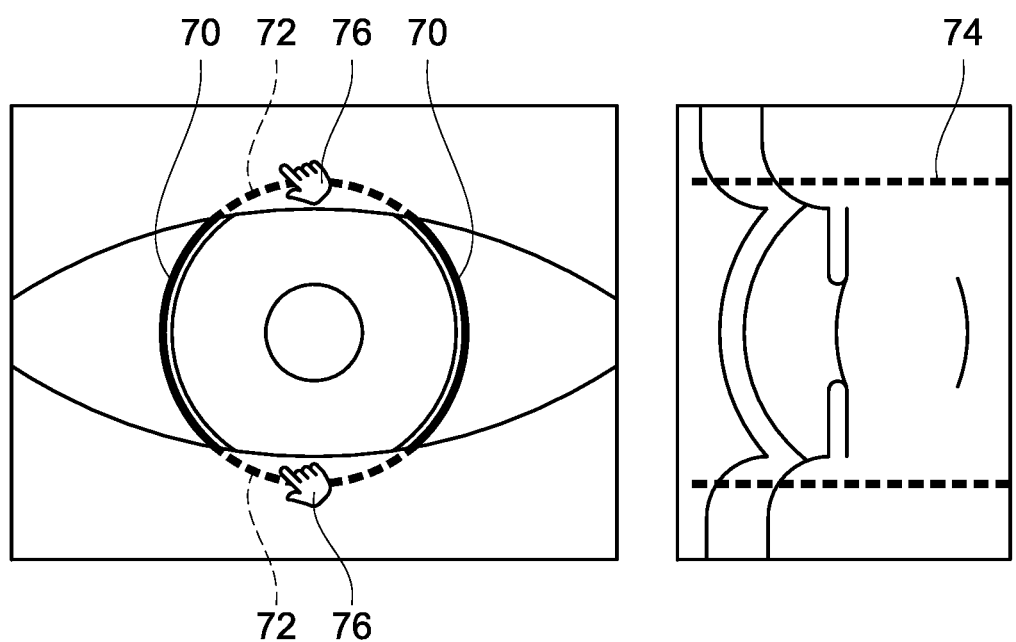

On the other hand, as shown in FIG. 8B, when the plurality of tomographic images includes image(s) in which the scleral spur SS has not been detected in step S14, portions of the circumference corresponding to positions where the scleral spur SS has been detected are displayed as the detected regions 70, while reminder portions of the circumference corresponding to positions where the scleral spur SS has not been detected are displayed as the non-detected regions 72. The detected regions 70 and the non-detected regions 72 may be identified by using, for example, the SS entire circumference fitting. In other words, the processor 60 calculates the reference circle by the SS entire circumference fitting by using a plurality of positions of the scleral spur SS, displays areas of the reference circle corresponding to positions where the scleral spur SS has been detected as the detected regions 70, and displays areas of the reference circle corresponding to positions where the scleral spur SS has not been detected as the non-detected regions 72. For example, as shown in FIG. 8B, when the eyelid sufficiently uncovers neither the upper part nor the lower part of the subject eye E, regions on left and right sides excluding the upper and lower parts become the detected regions 70, and the upper and lower parts become the non-detected regions 72. In the present embodiment, the detected regions 70 are displayed in solid lines, and the non-detected regions 72 are displayed in broken lines. As such, the detected regions 70 and the non-detected regions 72 are displayed in different manners, by which the examiner can easily distinguish the detected regions 70 and the non-detected regions 72.

Tomographic images of cross sections of the subject eye E including a corneal apex and being parallel to a Y-axis and Z-axis (see FIGS. 1 and 2) are displayed on the touch panel 56 as well as the image of the anterior eye part (specifically, the image of the anterior eye part on which the detected region(s) 70 and the non-detected region(s) 72 of the scleral spur SS are overlapped). The processor 60 overlaps line segments 74 which indicate positions of the scleral spur SS on the tomographic images displayed on the touch panel 56. Specifically, as shown in FIG. 7B, when the upper and lower parts of the subject eye E are the detected region 70, the line segments 74 are displayed in the tomographic images at positions corresponding to the detected region 70 displayed in the image of the anterior eye part. As such, in the tomographic images, the scleral spur SS is positioned on the line segments 74. On the other hand, as shown in FIG. 8B, when the upper and lower parts of the subject eye E are the non-detected regions 72 (or when one of the upper or lower part of the subject eye E is the non-detected region 72), the line segments 74 are displayed at positions corresponding to positions where the non-detected regions 72 of the image of the anterior eye part are displayed (i.e., positions on the reference circle). Thus, the line segments 74 are displayed at positions where the subject eye E has not been captured in the tomographic images.

Next, the processor 60 determines whether or not the non-detected region 72 is included in the image of the anterior eye part displayed in step S16 (S18). When the non-detected region 72 is not included in the image of the anterior eye part (NO in step S18), it can be determined that the tomographic images of the scleral sur SS are acquired over its entire circumference (see FIG. 7B). Due to this, the processor 60 terminates the processes of acquiring the image of the scleral spur SS of the subject eye E.

On the other hand, when the non-detected region 72 is included in the image of the anterior eye part (YES in step S18), it can be determined that there still is a portion in which the tomographic images of the scleral spur SS have not been acquired in its circumferential direction. In this case, as shown in FIG. 8B, the processor 60 displays marks 76 informing the presence of the non-detected regions 72 on the touch panel 56 (S20). For example, in FIG. 8B, the non-detected regions 72 are respectively present at the upper and lower parts of the subject eye E. Due to this, the processor 60 displays the marks 76 each indicating the non-detected region 72 at the upper part and at the lower part. Due to this, the examiner can be informed which regions of the subject eye E are not captured, and be urged to recapture the non-detected regions 72. Thus, the examiner can accurately identify the regions of the subject eye E which have not been captured, by which the number of times the subject eye E needs to be recaptured can be reduced. According to the marks 76 as informed, the examiner recaptures the tomographic images of the anterior eye part of the subject eye E so that the non-detected regions 72 can be captured. For example, when the mark 76 which indicates the upper part of the subject eye E is displayed, the examiner captures the subject eye E by causing the eyelid to uncover the upper part of the subject eye E. When the mark 76 which indicates the upper part of the subject eye E and the mark 76 which indicates the lower part of the subject eye E are both displayed, the examiner captures the subject eye E by causing the eyelid to uncover the upper and lower parts of the subject eye E, or captures the subject eye E by causing the eyelid to uncover one of the upper or lower parts of the subject eye E.

In the present embodiment, the marks 76 which indicate the non-detected regions 72 are displayed, but a configuration thereof is not limited to such a configuration. The examiner may be informed of the presence of the non-detected regions 72, and the non-detected regions 72 may be displayed in a manner which can more easily draw attentions than the detected regions 70. For example, the detected regions 70 and the non-detected regions 72 may be displayed in different colors (for example, the detected regions 70 may be displayed in green, and the non-detected regions 72 may be displayed in red) or only the non-detected regions 72 may blink. Further, instead of displaying the marks 76 which indicate the non-detected regions 72 (or in addition to displaying the marks 76), the presence of the non-detected regions 72 may be informed by a voice announcement, for example, "please recapture upper and lower parts".

Next, the processor 60 determines whether or not an instruction for starting an examination to acquire the tomographic images of the subject eye E has been inputted (S22). In other words, the processor 60 determines whether or not the instruction to recapture the tomographic images of the subject eye E has been inputted by the examiner. When the instruction for starting the examination has not been inputted (NO in step S22), the processor 60 waits until the instruction for starting the examination is inputted. On the other hand, when the instruction for starting the examination has been inputted (YES in step S22), the processor 60 acquires the tomographic images of the anterior eye part of the subject eye E (S24), and detects the scleral spur SS in each of the acquired tomographic images (S26). Since the processes of step S24 and step S26 are the same as the above-described step S12 and step S14, respectively, the detailed explanations thereof will be omitted.

Figure 9:
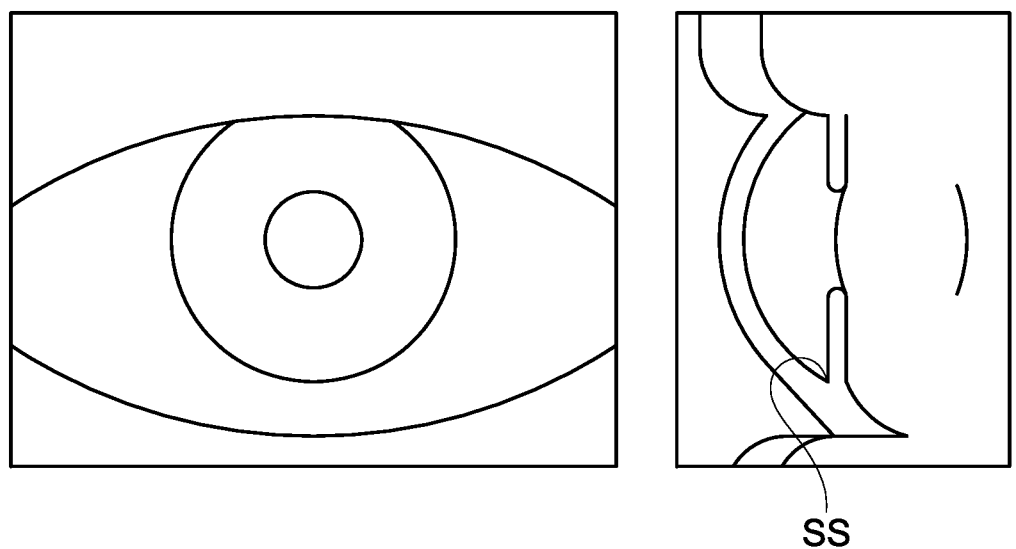
FIG. 9 schematically shows an image of the anterior eye part and its tomographic image captured in a state where the eyelid uncovers the lower part of the subject eye.

Next, the processor 60 executes matching of the image of the anterior eye part acquired from the tomographic images acquired in step S12 (hereinafter referred to as a first captured image) and the image of the anterior eye part acquired from the tomographic images acquired in step S24 (hereinafter referred to as a second captured images) (S28). The first captured image and the second captured image differ in their captured ranges of the subject eye E. For example, a central part excluding the upper and lower parts of the subject eye E is captured in the first captured image, while the lower part and the central part excluding the upper part of the subject eye E are captured in the second captured image as shown in FIG. 9. The processor 60 matches positions of the first captured image and the second captured image by using a common portion between a captured range of the first captured image and a captured range of the second captured image. Due to this, in a combining process which will be described later, displacement between the first captured image and the second captured image can be prevented from occurring.

A method of the matching is not particularly limited, and a well-known method thereof can be used. For example, the matching can be executed by using the following method. First, the processor 60 generates a two-dimensional tomographic image for each scan angle for each of the first captured image and the second captured image. A corneal apex is to be included in each generated two-dimensional tomographic image. Next, the processor 60 executes pattern matching of a plurality of two-dimensional tomographic images acquired from the first captured image and a plurality of two-dimensional images acquired from the second captured image, and determines an angle difference where a gap therebetween becomes minimum. Specifically, in a state where positions of the corneal apex in the first captured image and the corneal apex in the second captured image are matched, the processor 60 calculates respective luminance differences between each two-dimensional tomographic image acquired from the plurality of two-dimensional tomographic images and a corresponding one of the plurality of two-dimensional tomographic images acquired from the second captured image while changing an angle where datum line of the first captured image (a straight line which passes the corneal apex) and a datum line of the second captured image (a straight line which passes the corneal apex), and acquires a sum of these calculated luminance differences. When the luminance differences are calculated, the calculation is carried out by comparing respective luminance difference information of the anterior surface of the cornea of two-dimensional tomographic images corresponding to each other. Then, an angle difference where the sum of the luminance differences becomes minimum (an angle at which the datum line of the first captured image and the datum line of the second captured image meet) is determined, and this angle difference is determined as an angular displacement between the first captured image and the second captured image (displacement of a scan angle between the two captured images). Then, the positions of the first captured image and the second captured image are matched by giving consideration to the determined angular displacement (displacement of a scan angle).

The matching may be executed by using the SS entire circumference fitting. Specifically, the processor 60 at first calculates the reference circle by using the SS entire circumference fitting for each of the first captured image and the second captured image. Next, the processor 60 calculates gaps between the reference circle and respective positions of the detected scleral spur SS for the first captured image, and sets an angle where a sum of the gaps become minimum as a displacement angle of the first captured image. Further, the processor 60 calculates gaps between the reference circle and respective positions of the detected scleral spur SS for the second captured image, and sets an angle where a sum of the gaps become minimum as a displacement angle of the second captured image. Then, the positions of the first captured image and the second captured image in XY directions are matched so that centers of the reference circles of the two images match, and the positions of the first captured image and the second captured image are matched in an angle direction by displacing the first captured image by the displacement angle of the first captured image and displacing the second captured image by the displacement angle of the second captured image.

The matching may be executed by using the image of the anterior eye part. Specifically, the processor 60 at first respectively identifies an iris of the subject eye E for the image of the anterior eye part corresponding to the first captured image and the image of the anterior eye part corresponding to the second captured image. Next, the processor 60 executes the matching so that patterns of the identified respective irises match, and matches the positions of the first captured image and the second captured image. For example, the processor 60 extracts the characteristic pattern of the iris identified from the first captured image and extracts the characteristic pattern of the iris identified from the second captured image. Then, respective micromortion angles and amounts of movement of the first captured image and the second captured image are identified so that the characteristic pattern extracted from the first captured image and the characteristic pattern extracted from the second captured image are matched, and the two captured images are matched in position.

The matching may be executed by using measured data of the subject eye E (e.g., a measurement parameter which characterizes the subject eye E). An angle opening distance (AOD) may be employed as the measurement data, for example, but a type of measurement data to be employed is not particularly limited. For example, at first, the processor 60 acquires AOD data acquired from the first captured image and AOD data acquired from the second captured image. The pair of AOD data match in parts where the captured ranges are in common. Due to this, the processor 60 offsets one of the pair of AOD data (or both) so that the parts where the pair of AOD data match overlap. Due to this, the first captured image and the second captured image are matched in position.

Next, the processor 60 replaces the non-detected region(s) 72 in the first captured image with corresponding region(s) in the second captured image, and combines the two captured images (S30). In other words, the processor 60 cuts out the region(s) corresponding to the non-detected region(s) 72 in the first captured image from the second captured image, and combine the cut-out region(s) with the detected region 70 of the first captured image. For example, as shown in FIG. 8B, in supposing that the non-detected regions 72 of the first captured image are at the upper and lower parts of the subject eye E, and the eyelid uncovers the lower part of the subject eye E but does not uncover the upper part thereof in the second capturing. In other words, in supposing that the scleral spur SS at the lower part of the subject eye E is captured in the second captured image, while the scleral spur SS at the upper part of the subject eye E is not captured. In this case, the processor 60 cuts out both the region corresponding to the non-detected region 72 at the upper part of the first captured image and the region corresponding to the non-detected region 72 at the lower part of the non-detected region 72 from the second captured image, and combines the two regions with the detected regions 70 of the first captured image. Then, an image in which the scleral spur SS at the lower part of the subject eye E is captured together with the scleral spur SS at the right and left parts of the subject eye E (that is, an image in which only the scleral spur SS at the upper portion of the subject eye E is not captured) is generated.

The processor 60 may cut out only portion(s) which has (have) been detected in the second captured image and combine the portion(s) with the first captured image. Specifically, the processor 60 identifies the detected region(s) 70 and the non-detected region(s) 72 in the second captured image. Next, the processor 60 cuts out only region(s) corresponding to the non-detected region(s) 72 in the first captured image among the detected region(s) 70 in the second captured image, and combines the cut-out region(s) with the first captured image. In other words, in the above example, the processor 60 cuts out only a region corresponding to the non-detected region 72 at the lower part of the first captured image from the second captured image. Then the processor 60 combines the region cut out from the second captured image (that is, the region corresponding to the non-detected region 72 at the lower part of the first captured image) with the detected region 70 and the upper non-detected region 72 of the first captured image.

Next, the processor 60 displays the combined image generated in step S30 on the touch panel 56, and overlaps the detected region(s) 70 and the non-detected region(s) 72 of the combined image with the combined image, and displays the resulting image (S32). Then, the processor 60 determines whether or not the combined image generated in step S30 includes the non-detected region(s) 72 (S34). When the combined image includes the non-detected region(s) 72 (YES in step S34), the processor 60 returns to step S20 and repeats the processes of step S20 to step S34. On the other hand, when combined image does not include the non-detected region 72 (NO in step S34), the processor 60 terminates the process of acquiring the image of the scleral spur SS of the subject eye E.

Figure 10:
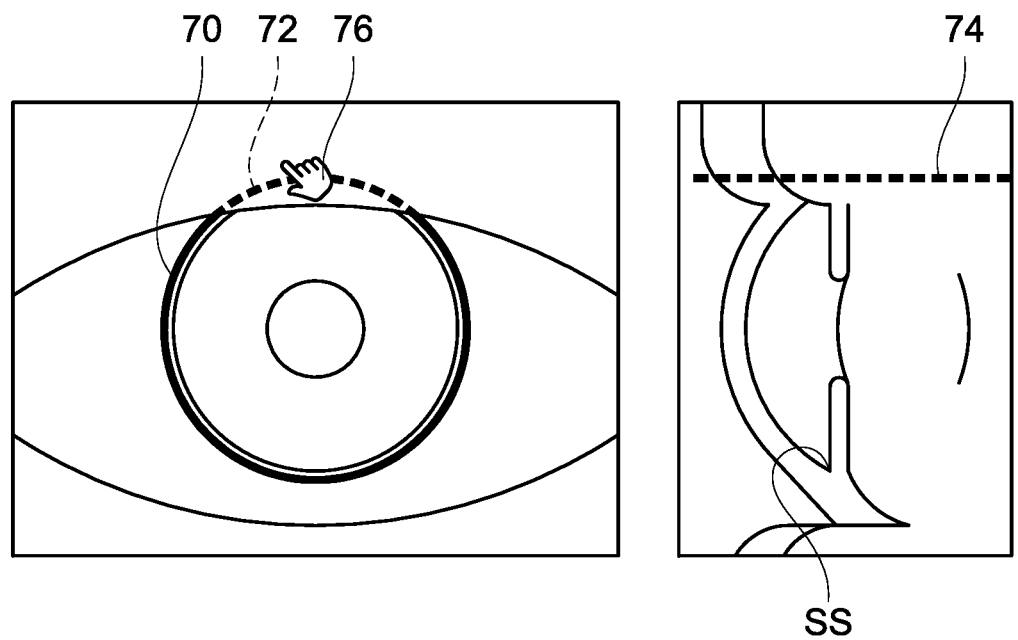
FIG. 10 schematically shows an image in which a region of a second captured image corresponding to a non-detected region of a first captured image is combined with the first captured image form which the non-detected region thereof is omitted.
Figure 11:
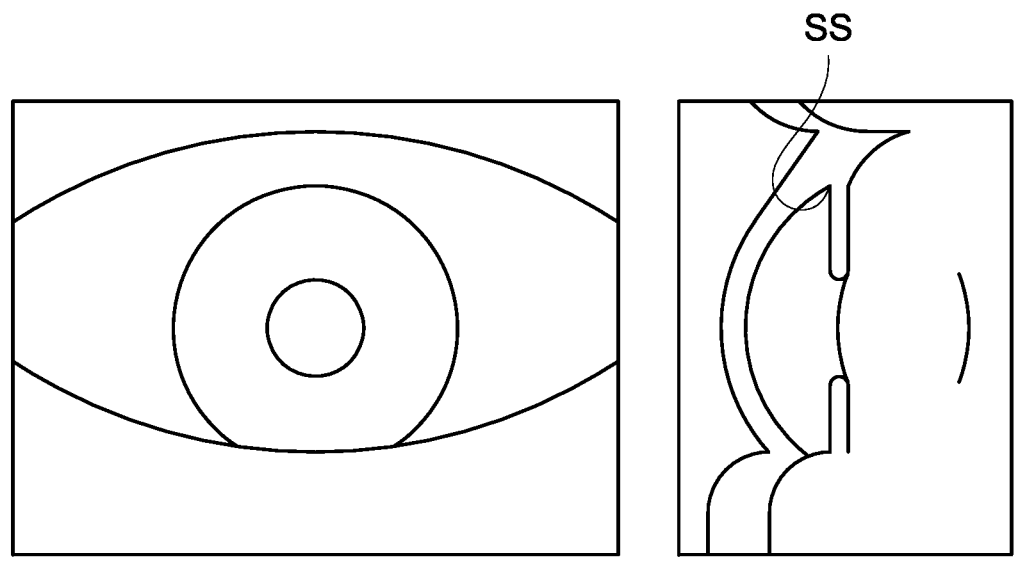
FIG. 11 schematically shows an image of the anterior eye part and its tomographic image captured in a state where the eyelid uncovers the upper part of the subject eye.

For example, when the first captured image has the two non-detected regions 72 at the upper and lower parts of the subject eye E as shown in FIG. 8B and the eyelid uncovers the lower part of the subject eye E but does not uncover the upper part thereof in the second capturing as shown in FIG. 9, the image generated in step S30 includes the non-detected region 72 at the upper part of the subject eye E. In this case, the processor 60 returns to step S20 and causes the touch panel 56 to display the mark 76 instructing the presence of the non-detected region 72 at the upper part of the subject eye E as shown in FIG. 10. Due to this, the examiner can be informed that the scleral spur SS at the upper part of the subject eye E is not captured. And, the examiner recaptures the subject eye E in a state where the eyelid uncovers the upper part of the subject eye E according to the instruction. Then, as shown in FIG. 11, the scleral spur SS at the upper part of the subject eye E is captured. After this, the processor 60 executes the processes of step S22 to step S34, cuts out a region corresponding to the non-detected region 72 at the upper part of the subject eye E from a third captured image, and combines the region which has been cut out from the third captured image and the combined image generated in the previous step S30. Then, an image in which the scleral spur SS is captured over its entire circumference is generated as shown in FIG. 7A. As such, even though an image in which the scleral spur SS is captured over its entire circumference cannot be captured at the first capturing, an image in which a desirable area is captured can be generated by combining a plurality of images.

When the ophthalmic apparatus 1 of the present embodiment is used, the image in which the scleral spur SS is captured over its entire circumference can be generated by combining images captured for a plurality of times. Due to this, there is no need capturing the subject eye E many times until a desirable image is captured, thus the number of capturing needed to capture the desirable image can be reduced. Further, since the examiner can be informed of the presence of the non-detected region(s) 72, the examiner can appropriately identify region(s) remained to be recaptured. Due to this, the number of capturing needed to capture the desirable image can be reduced. Since the number of capturing can be reduced as such, burden on the examinee can be reduced.

Although the image in which the scleral spur SS is captured over its entire circumference is acquired (generated) in the present embodiment, a configuration thereof is not limited to such a configuration. A target part to be captured is not limited to the scleral spur SS, but it may be any part or region in the subject eye E. For example, the target part may be an anterior chamber angle portion including the scleral spur SS, or may be an anterior eye part including a cornea. Further, the target part may be a region including tissues of the subject eye E excluding the anterior eye part. Further, the combined image may not be generated to include the entire target part such as the scleral spur SS, and the entire target part may not be included as long as the desired area is included. For example, the combined image may not be generated to include an entire target part in its circumferential direction (i.e., 360°), and it may be generated to include the desired area thereof in its circumferential direction (e.g., 270° or greater).

Notes for the ophthalmic apparatus 1 disclosed in the embodiment will be described. The interference optical system 14 and the K-clock generator 50 are examples of "image capturing unit", the touch panel 56 is an example of "display unit" and "informing unit", and the processor 60 is an example of "processor".

Specific examples of the disclosure herein have been described in detail, however, these are mere exemplary indications and thus do not limit the scope of the claims. The art described in the claims includes modifications and variations of the specific examples presented above. Technical features described in the description and the drawings may technically be useful alone or in various combinations, and are not limited to the combinations as originally claimed.

What is claimed is:
1. An ophthalmic apparatus comprising:
an image capturing unit configured to capture a target part of a subject eye;
a processor; and
a memory storing computer-readable instructions therein, wherein the computer-readable instructions, when executed by the processor, cause the ophthalmic apparatus to execute:
acquiring a first image of the target part captured at a first timing by the image capturing unit and a second image of the target part captured at a second timing different from the first timing, the first image being a front image or a tomographic image, the second image being a front image when the first image is the front image and the second image being a tomographic image when the first image is the tomographic image; and
combining the first image with the second image to generate one combined image of the target part.

2. The ophthalmic apparatus according to claim 1, further comprising a display unit configured to display images of the target part including the combined image of the target part.

3. The ophthalmic apparatus according to claim 1, wherein
the first image is an image that is captured when an eyelid uncovers a first region of the target part,
the second image is an image that is captured when the eyelid uncovers a second region of the target part, and
the second region is different from the first region.

4. The ophthalmic apparatus according to claim 1, wherein in the combining, the first image and the second image are combined by matching positions of a common portion captured respectively in the first image and the second image.

5. The ophthalmic apparatus according to claim 1, wherein
the computer-readable instructions, when executed by the processor, further cause the ophthalmic apparatus to execute identifying a non-detected region in the first image, the non-detected region being a part of the target part and a region in which no image is captured, and
in the combining, a portion of the second image corresponding to the non-detected region of the first image is combined with a portion of the first image where the target part is not detected.

6. The ophthalmic apparatus according to claim 5, further comprising an informing unit configured to inform presence of the non-detected region when an image captured by the image capturing unit includes the non-detected region.

7. The ophthalmic apparatus according to claim 6, wherein
the informing unit is further configured to:
instruct to open an eyelid to uncover an upper part of the subject eye when the non-detected region is located in the upper part of the subject eye;
instruct to open the eyelid to uncover a lower part of the subject eye when the non-detected region is located in the lower part of the subject eye; and
instruct to open the eyelid to uncover the upper and lower parts of the subject eye when the non-detected regions are located in the upper and lower parts of the subject eye.

8. An ophthalmic apparatus configured to measure a target part of a subject eye, the ophthalmic apparatus comprising:
an image capturing unit configured to capture the target part;
a processor;
a memory storing computer-readable instructions therein; and
an informing unit,
wherein
the computer-readable instructions, when executed by the processor, cause the ophthalmic apparatus to execute:
acquiring an image of the target part captured by the image capturing unit; and
identifying a non-detected region in the image of the target part, the non-detected region being a part of the target part and a region in which no image is captured, and
the informing unit is configured to inform presence of the identified non-detected region.

* * * * *